United States Patent
Juvinall et al.

(10) Patent No.: US 6,903,814 B1
(45) Date of Patent: Jun. 7, 2005

(54) CONTAINER SEALING SURFACE INSPECTION

(75) Inventors: John W. Juvinall, Ottawa Lake, MI (US); Brian A. Langenderfer, Sylvania, OH (US); James A. Ringlien, Maumee, OH (US); Timothy J. Nicks, Maumee, OH (US); William H. Anderson, Sylvania, OH (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 9 days.

(21) Appl. No.: 10/379,924

(22) Filed: Mar. 5, 2003

(51) Int. Cl.[7] .............................................. G01N 21/90
(52) U.S. Cl. ................. 356/240.1; 356/428; 250/223 B
(58) Field of Search ...................... 356/239.1–239.2, 356/239.3, 239.4, 240.1, 239.7, 237.1, 426, 428; 250/223 B, 223 R

(56) References Cited

U.S. PATENT DOCUMENTS

| | | | |
|---|---|---|---|
| 3,880,750 A | 4/1975 | Butler et al. | |
| 4,213,042 A | 7/1980 | Beach et al. | |
| 4,213,702 A | 7/1980 | Bryant et al. | |
| 4,701,612 A | 10/1987 | Sturgill | |
| 4,758,084 A | 7/1988 | Tokumi et al. | |
| 4,775,889 A | 10/1988 | Yoshida | |
| 4,811,251 A | 3/1989 | Minato | |
| 4,929,828 A | 5/1990 | Claypool | |
| 4,945,228 A | 7/1990 | Juvinall et al. | |
| 4,959,538 A | 9/1990 | Swart | |
| 5,200,801 A | 4/1993 | Juvinall et al. | |
| 5,414,939 A | 5/1995 | Wuagaman | |
| 5,489,987 A | 2/1996 | Ringlien | |
| 5,617,204 A | 4/1997 | Hinata | |
| 5,896,195 A | 4/1999 | Juvinall et al. | |
| 6,025,909 A | 2/2000 | Juvinall et al. | |
| 6,104,482 A | 8/2000 | Brower et al. | |
| 6,172,748 B1 | 1/2001 | Sones et al. | |
| 6,175,107 B1 | 1/2001 | Juvinall | |
| 6,211,952 B1 | 4/2001 | Weiland et al. | |
| 6,256,095 B1 | 7/2001 | Ringlien | |
| 6,275,287 B1 | 8/2001 | Watanabe | |
| 6,365,906 B1 * | 4/2002 | Spangenberg et al. | ... 250/559.3 |
| 6,448,549 B1 | 9/2002 | Safaee-Rad | |
| 6,473,170 B2 | 10/2002 | Schafer | |
| 2001/0048524 A1 | 12/2001 | Sones | |
| 2002/0078769 A1 | 6/2002 | Giometti | |
| 2003/0034227 A1 | 2/2003 | Gerber et al. | |

FOREIGN PATENT DOCUMENTS

| | | |
|---|---|---|
| EP | 0 324 285 A2 | 7/1989 |
| JP | 57007547 A | 1/1982 |
| JP | 58034348 A | 2/1983 |
| JP | 62113050 A | 5/1987 |
| JP | 02010254 A | 1/1990 |
| JP | 03024447 A | 2/1991 |
| WO | WO 90/02937 | 3/1990 |

* cited by examiner

Primary Examiner—Hoa Q. Pham

(57) ABSTRACT

Apparatus for inspecting a container finish includes at least one light source for directing light energy onto the sealing surface of a container. At least one light sensor is disposed to receive light energy reflected from the sealing surface of the container, and is responsive to such reflected light energy to provide signals indicative of the level of the sealing surface at at least four points on the sealing surface spaced from each other around the axis of the container finish. An information processor is responsive to such signals for detecting variations in level at the sealing surface of the container. In the preferred embodiments of the invention, the points on the sealing surface from which reflected energy is received at the sensor are at a nominal angle of 90° from each other. The information processor preferably is responsive to such signals for detecting warp, dip, off-level and overall height variations at the sealing surface.

20 Claims, 7 Drawing Sheets

CONTAINER SEALING SURFACE INSPECTION

The present invention is directed to inspection of containers, and more particularly to an apparatus and method for measuring variations in level at the sealing surface of a container.

BACKGROUND AND SUMMARY OF THE INVENTION

In the manufacture of containers such as glass or plastic bottles and jars, the container typically is formed with a finish having an axis and means for securing a closure to the finish. The finish has an open mouth surrounded by an axially facing sealing surface for sealing engagement with a closure applied to the container. Manufacturing anomalies can occur at the container sealing surface, such as a warp, a dip or an off-level condition, also known as a cocked sealing surface. A "warp" at the sealing surface generally refers to departure of the sealing surface from a planar configuration. A "dip" at the sealing surface refers to an unfilled area at the sealing surface, typically narrower and deeper than a warp. "Off-level" refers to a tilt of the average plane of the sealing surface from an orientation perpendicular to the finish axis. Warp, dip and off-level anomalies at the sealing surface can occur in combinations, and can affect the ability of an automatic capping machine to apply a closure to the finish and/or to the ability of the closure to form an effective seal against the sealing surface. Other variations in sealing surface level include over-height and under-height at the sealing surface, which refer to departure of the sealing surface from a nominal height for the container under inspection.

U.S. Pat. No. 5,489,987, assigned to the assignee of the present application, discloses an apparatus and method for inspecting the sealing surface of a container, which includes a light source positioned to direct a narrow beam of light energy at an acute angle onto the sealing surface of a container. A light sensor is disposed to receive the narrow beam of light energy reflected from the sealing surface, and provides an output that varies as a function of the position of incidence of the reflected beam on the sensor. The sensor is coupled to associated electronics for providing information indicative of container height and a signal for controlling separation of the container from a conveyor system when the height of the container, the warp or dip at the container sealing surface, or an off-level condition at the sealing surface exceeds predetermined standards. In one embodiment, a light source/sensor pair is provided at diametrically opposed sides of the container finish. Dips at the sealing surface and an off-level container finish are identified and measured as a function of a difference between the sensor output signals, while a warped sealing surface is identified and measured as a function of a sum of the sensor output signals. Height of the container and variations in height between successive containers may be determined as a function of the output signal from either or both of the sensors. U.S. Pat. Nos. 5,896,195 and 6,025,909, also assigned to the assignee of the present application, disclose a container sealing surface inspection apparatus and method in which the narrow beam from the light source is line-shaped, having an elongated dimension chordally of the container finish for accommodating wobble at the container finish.

The present invention embodies a number of aspects that may be implemented separately from or more preferably in combination with each other.

Apparatus for inspecting a container finish in accordance with a first aspect of the present invention includes at least one light source for directing light energy onto the sealing surface of a container. At least one light sensor is disposed to receive light energy reflected from the sealing surface of the container, and is responsive to such reflected light energy to provide signals indicative of the level of the scaling surface at at least four predetermined points on the sealing surface spaced from each other around the axis of the container finish. An information processor is responsive to such signals for detecting variations in level at the sealing surface of the container. In the preferred embodiments in accordance with this aspect of the invention, the predetermined points on the sealing surface from which reflected energy is received at the sensor are at a nominal angle of 90° from each other. The information processor preferably is responsive to such signals for detecting warp, dip, off-level and overall height variations at the sealing surface. In the preferred embodiments, the container is moved (e.g., rotated or moved laterally) so that the spaced inspection points effectively sweep the sealing surface. A less preferred alternative would be for the inspection apparatus to move while the container is stationary so that the at least one sensor sweeps the container sealing surface. The motions could be combined, so that a rotating inspection apparatus moves laterally, for example, to follow a laterally moving container.

Apparatus for inspecting the sealing surface of a container finish in accordance with another aspect of the invention includes a first light source for directing light energy onto a first point on the sealing surface of the container, and a first light sensor for receiving light energy reflected from the first point on the sealing surface to provide a signal indicative of level at the first point. A second light source directs light energy onto a second point on the sealing surface circumferentially spaced from the first point around the axis of the container finish, and a second light sensor receives light energy reflected from the second point to provide a signal indicative of level at the second point. An information processor is responsive to the signals for detecting variations in level at the first and second points on the sealing surface. The first light source/sensor pair and the second light source/sensor pair are simultaneously adjustable with respect to the axis of the container finish to accommodate inspection of container finishes of differing diameters. In the preferred embodiments of this aspect of the invention having four light source/sensor pairs responsive to circumferentially spaced points on the container sealing surface, each light source/sensor pair is each provided in the form of a subassembled probe. The probes are disposed in opposed pairs that are simultaneously adjustable radially inwardly and outwardly with respect to the finish axis. In the preferred embodiment, one pair of probes is directly coupled to a threaded rod, and the other pair of probes is coupled to the rod through a cam plate and a cam shaft, so that rotation of the threaded rod simultaneously and equally adjusts all four probes with respect to the container axis.

Apparatus for inspecting the sealing surface of a container finish in accordance with a third aspect of the invention includes a first light source for directing light energy onto a first point on the sealing surface of the container, and a first light sensor for receiving light energy from the first source reflected from the first point to provide a first signal indicative of level at the first point on the sealing surface. A second light source directs light energy onto a second point on the sealing surface circumferentially spaced 90° from the first point around the axis of the container finish, and a second light sensor receives light energy from the second source reflected from the second point to provide a second signal indicative of level at the second point on the sealing surface. The container is rotated such that the finish and the sealing surface rotate about the axis of the finish. An information processor periodically scans the first and second sensors to provide a periodic signal that varies as a function of the first and second signals. The information processor is adapted to separate this periodic signal into first and second components, having respective periods of 180° and 360° of finish rotation, to determine off-level at the sealing surface as a function of the 360° component and to determine warp at the sealing surface as a function of the 180° component.

BRIEF DESCRIPTION OF THE DRAWINGS

The invention, together with additional objects, features, advantages and aspects thereof, will be best understood from the following description, the appended claims and the accompanying drawings, in which:

DETAILED DESCRIPTION OF PREFERRED EMBODIMENTS

Figure 1:
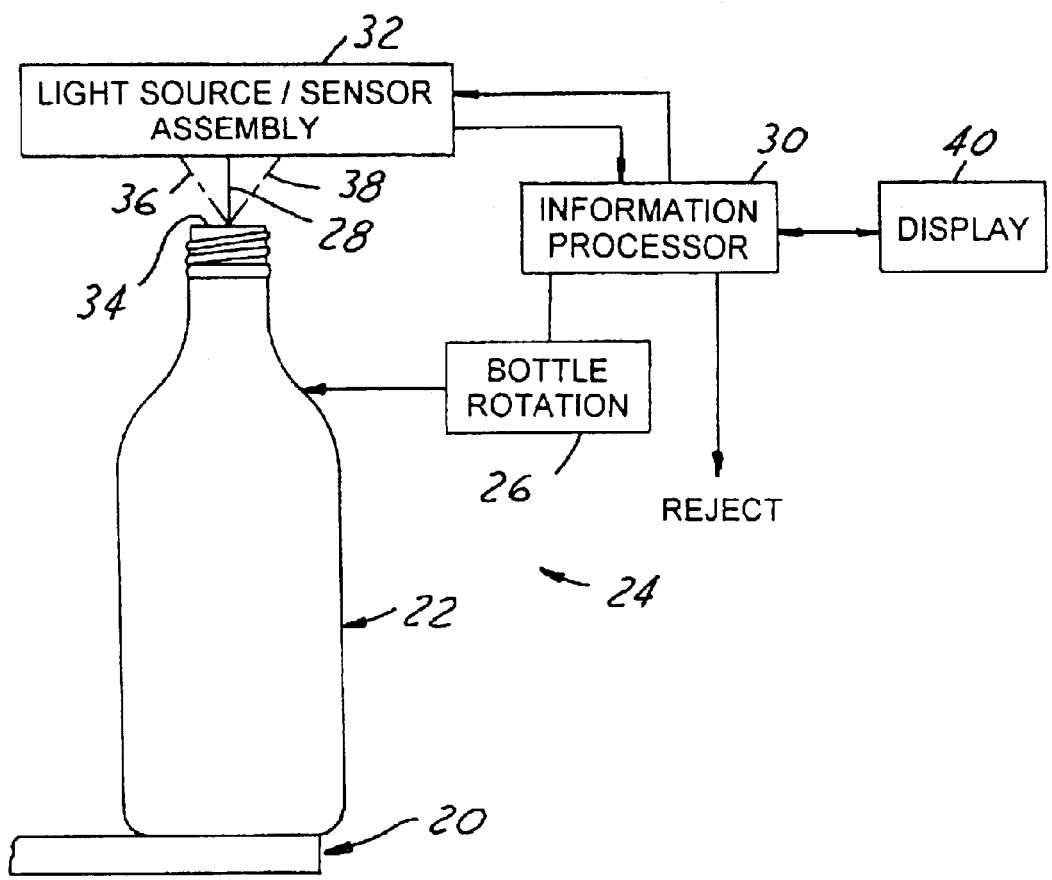
FIG. 1 is a schematic diagram of an apparatus for inspecting the sealing surface of containers in accordance with one exemplary presently preferred embodiment of the invention.

Referring to FIG. 1, a conveyor 20 is disposed and connected to a source of containers 22 to bring successive containers into position at a sealing surface inspection station 24. Conveyor 20 may take the form of a starwheel conveyor of the type illustrated in U.S. Pat. No. 4,230,219, for example, or of the type illustrated in U.S. application Ser. No. 09/679,584 filed Oct. 4, 2000. A container rotating device 26, such as a drive roller, is positioned to engage each container 22 in sequence at station 24, and to rotate the container around axis 28 while the container is held in position. (The apparatus of the present invention accommodates wobble at the sealing surface due to lateral or angular offset of the finish and/or sealing surface with respect to the axis of rotation. However, for purposes of simplifying the discussion, the axis 28 will be treated as the axis of the sealing surface and the container finish.) Bottle rotation device 26 is connected to an information processor 30 so that information processor 30 develops signals indicative of increments of container rotation. Such container rotation increments may comprise fixed increments of angular rotation, or more preferably fixed time increments as the container is rotated at constant velocity. A light source/sensor assembly 32 is positioned above the sealing surface 34 of container 22. Light source/sensor assembly 32 directs at least one beam 36 of light energy onto sealing surface 34, and receives at least one reflected beam 38 of light energy. Information processor 30 controls operation of assembly 32, and scans assembly 32, preferably at fixed time or spatial increments of container rotation, to receive signals indicative of the level of container finish 34. Information processor 30 may display such level information at an operator display 40, or may provide a signal to reject the container under inspection by removal from the conveyor line. Information from processor 30 may also be employed to feed data back to the forming equipment to correct variations found in the containers.

Figure 2:
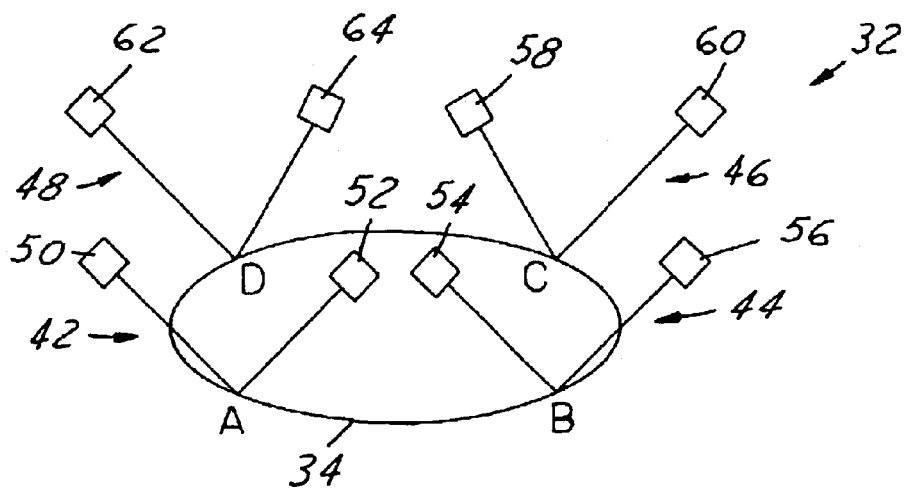
FIG. 2 is a schematic diagram of the light source/sensor pairs relative to the container sealing surface in one preferred embodiment of the invention.

FIG. 2 schematically illustrates light source/sensor assembly 32 in greater detail in accordance with one presently preferred embodiment of the invention. Light source/sensor assembly 32 includes four light source/sensor pairs 42, 44, 46, 48 for directing light energy onto and receiving light energy reflected from circumferentially spaced points A, B, C, D on sealing surface 34. Light source/sensor pair 42 includes a light source 50 for directing light energy onto sealing surface point A, and an associated sensor 52 for receiving light energy from source 50 reflected from sealing surface point A. Likewise, light source/sensor pair 44 includes a light source 54 and an associated sensor 56 for directing light energy onto and receiving light energy reflected from point B on sealing surface 34, light source/sensor pair 46 includes a light source 58 and a sensor 60 for directing light energy onto and receiving light energy reflected from point C on sealing surface 34, and light source/sensor pair 48 includes a light source 62 and associated sensor 64 for directing light energy onto and receiving light energy reflected from point D on sealing surface 34. Each light source 50, 54, 58, 62 preferably takes the form of a laser light source, such as a laser diode, for directing a collimated line-shaped light beam 66 (FIGS. 3 and 4) onto sealing surface 34.

Figure 3:
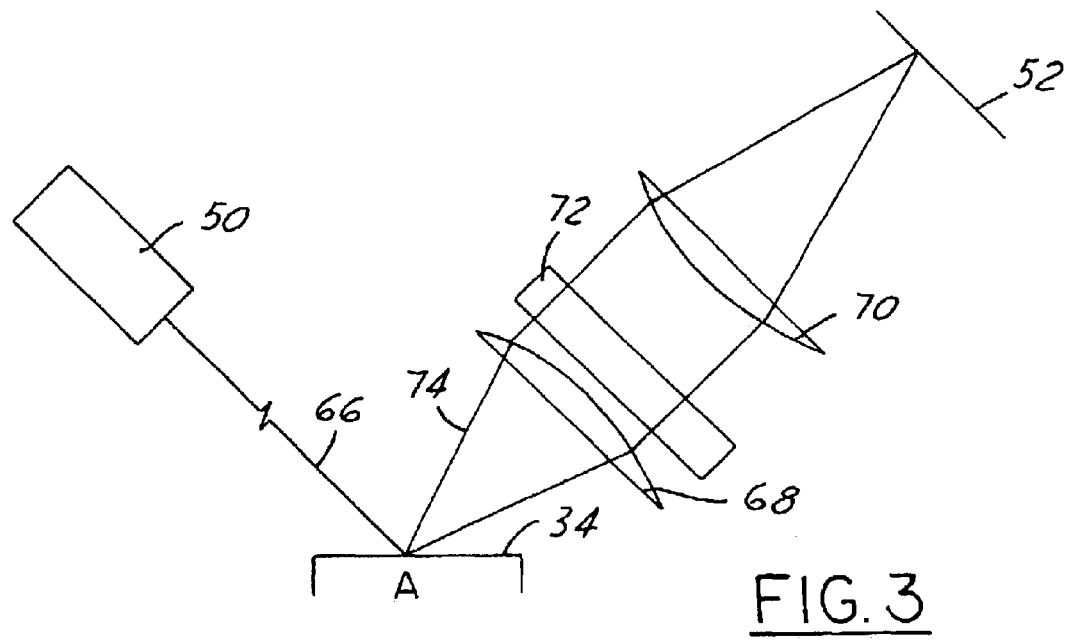
FIG. 3 is a side elevational schematic diagram of one light source/sensor pair in the embodiment of FIG. 2.
Figure 4:
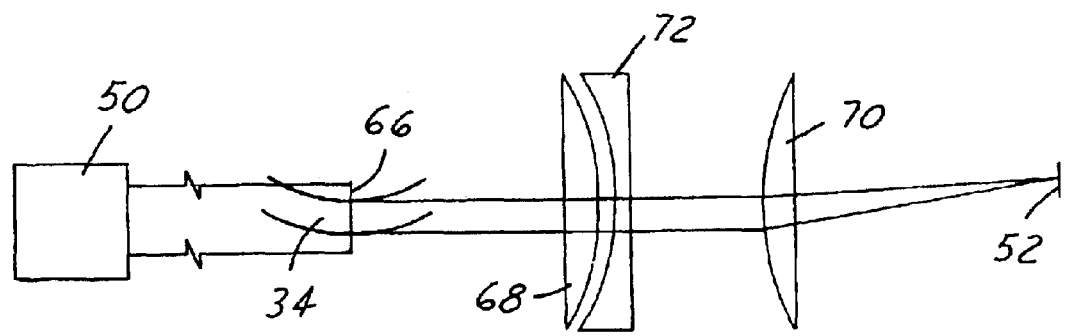
FIG. 4 is a top plan schematic diagram of the light source/sensor pair in FIG. 3.

FIGS. 3 and 4 schematically illustrate light source/sensor pair 50, 52 in detail, the remaining light source/sensor pairs being identical thereto except for positioning around the axis of the container finish. Light energy reflected from sealing surface 34 is directed onto sensor 52 through a lens arrangement that includes a pair of spherical lenses 68, 70 and an intermediate cylindrical lens 72. The purpose of lenses 68–72 is to select the light rays to be used for measurement purposes, and to exclude extraneous light as described in greater detail in U.S. Pat. No. 6,256,095. As an alternative, a single spherical lens and a single cylinder lens could be employed as disclosed in the noted patent. Sensor 52, preferably comprises a linear array sensor that provides an output signal to information processor 30 (FIG. 1) indicative of the position of incidence of reflected light beam 74 on the sensor, which in turn is indicative of the level of the sealing surface at reflection point A. Each linear array sensor is perpendicular to the longitudinal dimension of the associated line-shaped beam 66 and lies in a plane parallel to the axis of the container finish. As an alternative to a linear array sensor, sensor 52 may comprise an area array sensor or a lateral effect diode, for example. As another alternative, an area array sensor can be employed with no cylinder lens.

Figure 5:
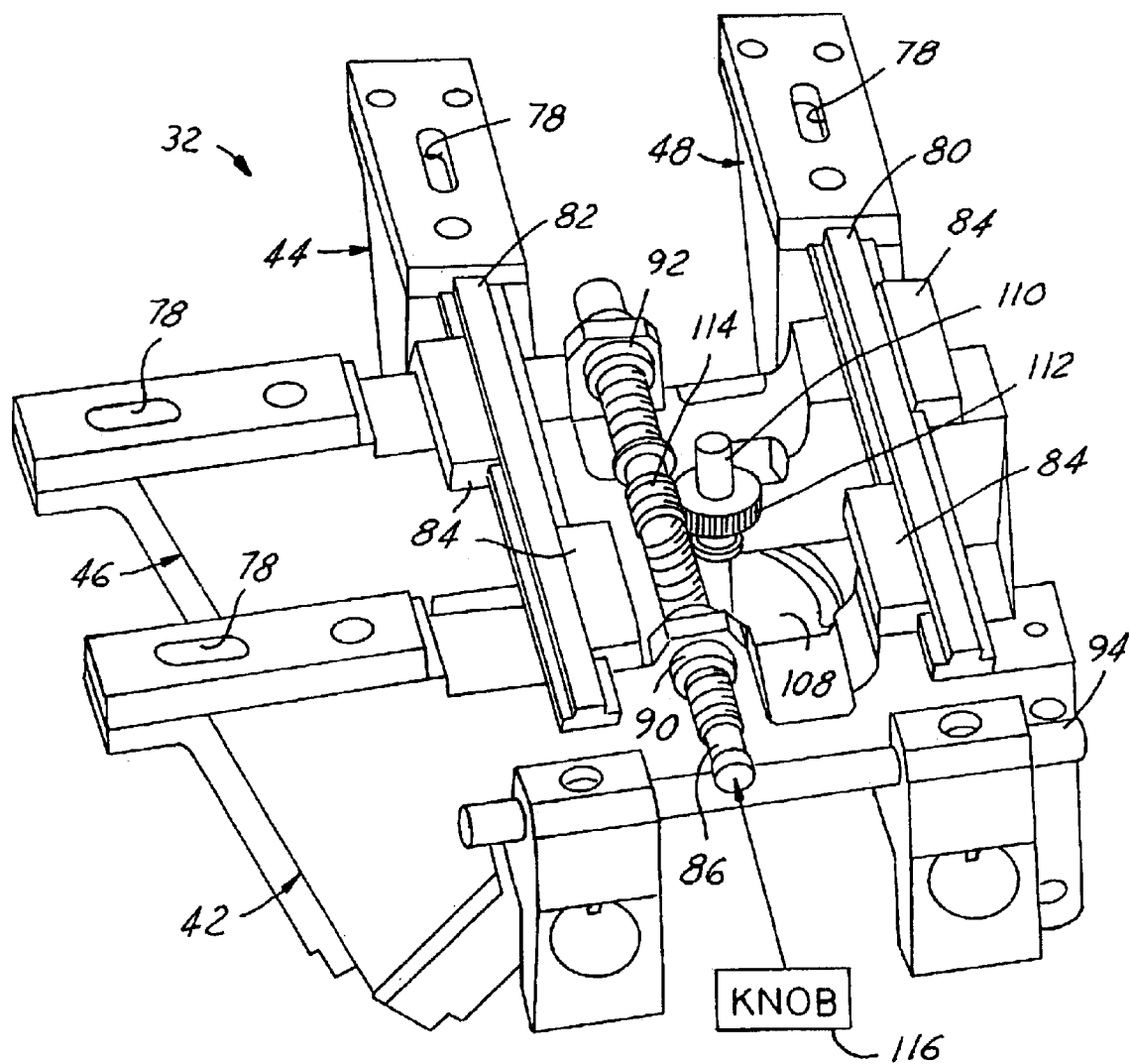
FIG. 5 is a top perspective view of the light source/sensor assembly illustrated schematically in FIG. 2.
Figure 6:
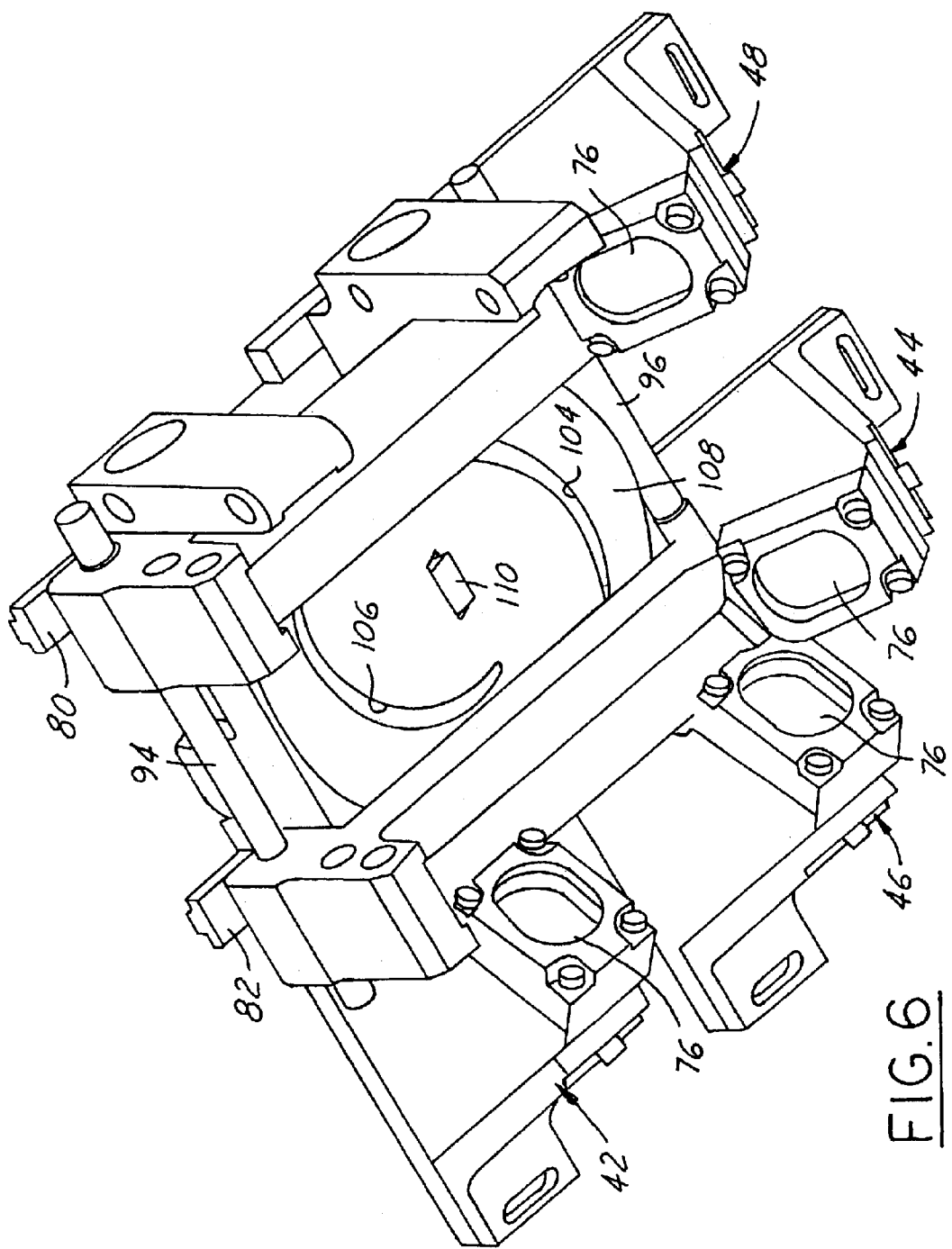
FIG. 6 is a bottom perspective view of the light source/sensor assembly in FIG. 5.
Figure 7:
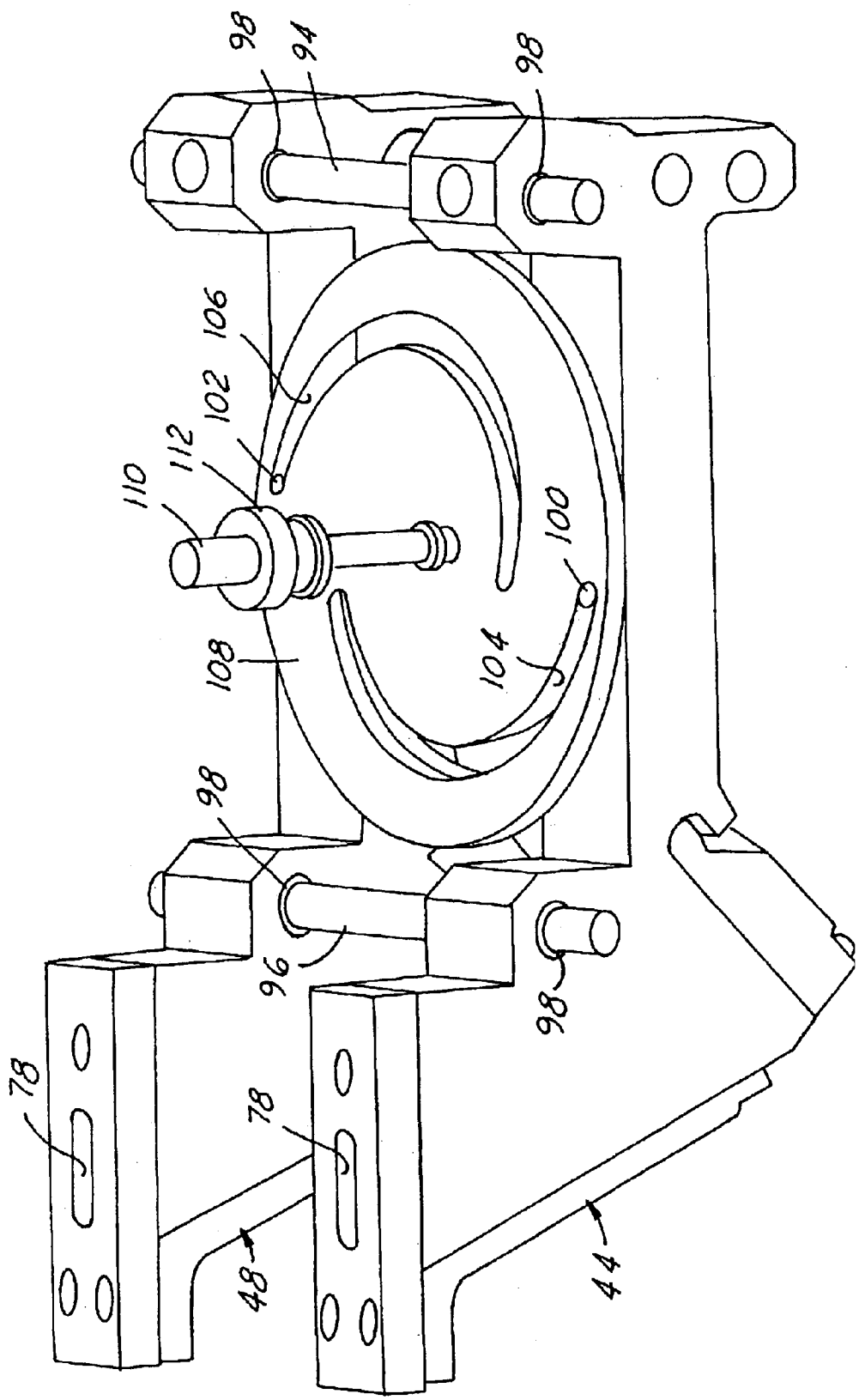
FIG. 7 is a top perspective view of a portion of the assembly illustrated in FIG. 5.

FIGS. 5–7 illustrate mechanical details of light source/sensor assembly 32. Each light source/sensor pair 42, 44, 46, 48 preferably is in the form of a subassembled optical probe, which are identified with corresponding reference numerals 42–48 in FIGS. 5–7 for purposes of clarity. Within each probe, there is a laser diode that directs a narrow line-shaped beam through a window onto the sealing surface of the container, and the reflected light energy is received through an input window 76 and thence through lenses 68–72 (FIGS. 3–4) onto the associated sensor. Each probe has an opening 78 for connection of the internal sensor to information processor 30 (FIG. 1). Probes 42, 46 are mounted by linear bearings 84 on a pair of spaced parallel slides or guide rails 80, 82. An externally threaded rod 86 extends through oppositely threaded bushings 90, 92 carried by upstanding legs on respective probes 42, 46. The ends of rod 86 that extend through bushings 90, 92 are threaded in opposite directions, so that rotation of rod 86 moves probes 42, 46 simultaneously and equally toward or away from each other depending upon the direction of rotation of rod 86.

Probes 44, 48 are mounted on a pair of spaced guide rails 94, 96 by associated linear bearings, such as sleeve bearings 98. Guide rails 94, 96 are parallel to each other, and orthogonal to slides 80, 82. Each probe 44, 48 has an upstanding pin 100, 102 that is received in an associated arcuate slot or opening 104, 106 in a cam plate 108. Openings 104, 106 are diametrically opposed and mirror images of each other, oppositely spiraling toward the axis of cam plate 108. A cam shaft 110 extends upwardly from the center of cam plate 108. A threaded gear 112 is disposed on shaft 110 in threaded engagement with a portion 114 (FIG. 5) of rod 86 disposed between the oppositely threaded end portions of the rod. Sides 80, 82 and guide rails 94, 96 are supported by overhanging support structure (not shown) so as to mount light source/sensor assembly in position at container inspection station 24 (FIG. 1).

Thus, rotation of threaded rod 86 not only moves probes 42, 46 in opposite directions, but also simultaneously moves probes 44, 48 in opposite directions by means of threaded gear 112, cam shaft 110, cam plate 108 and pins 100, 102 in cam plate openings 104, 106. Such simultaneous motions at the probes preferably are equal functions of rotation at rod 86. In other words, for a given angular rotation at rod 86 in one direction, all probes 42–48 move radially inwardly an equal amount, and for the same angular rotation at rod 86 in the opposite direction, all probes move radially outwardly the same amount. Threaded rod 86 may be connected to a knob 116 (FIG. 5) for manual rotation of the threaded rod and manual adjustment of the probe positions, or to a suitable servo motor for automated adjustment. Thus, the light source/sensor probes are simultaneously and equally adjustable with respect to each other and with respect to the axis of the finish for accommodating containers having differing finish diameters. If the container finish diameter exceeds the range of adjustment of light source/sensor assembly 32, two of the probes—e.g., probes 44, 48—may be removed and the inspection proceed on the basis of two rather than four reflected light signals.

In the preferred embodiments on the invention, measurement points A, B, C and D around sealing surface 34 are nominally spaced 90° from each other. The word "nominal" refers to the design height of the container under inspection, and to a sealing surface without warp, dip or off-level. The presence of sealing surface anomalies can affect the actual point of incidence and reflection of a measurement beam. For measurement of large finish diameters, it may be necessary to adjust probes 44, 48 so that measurements points B and D move together toward either point A or point C. Also, for large-diameter container finishes, it maybe necessary or desirable to remove probes 44, 48, and to proceed with container sealing surface inspection employing only probes 42, 46 and incidence/reflection points A and C spaced 180° from each other. All angular light source/sensor positions and incident/reflection point positions are nominal unless otherwise indicated.

Figure 8A:
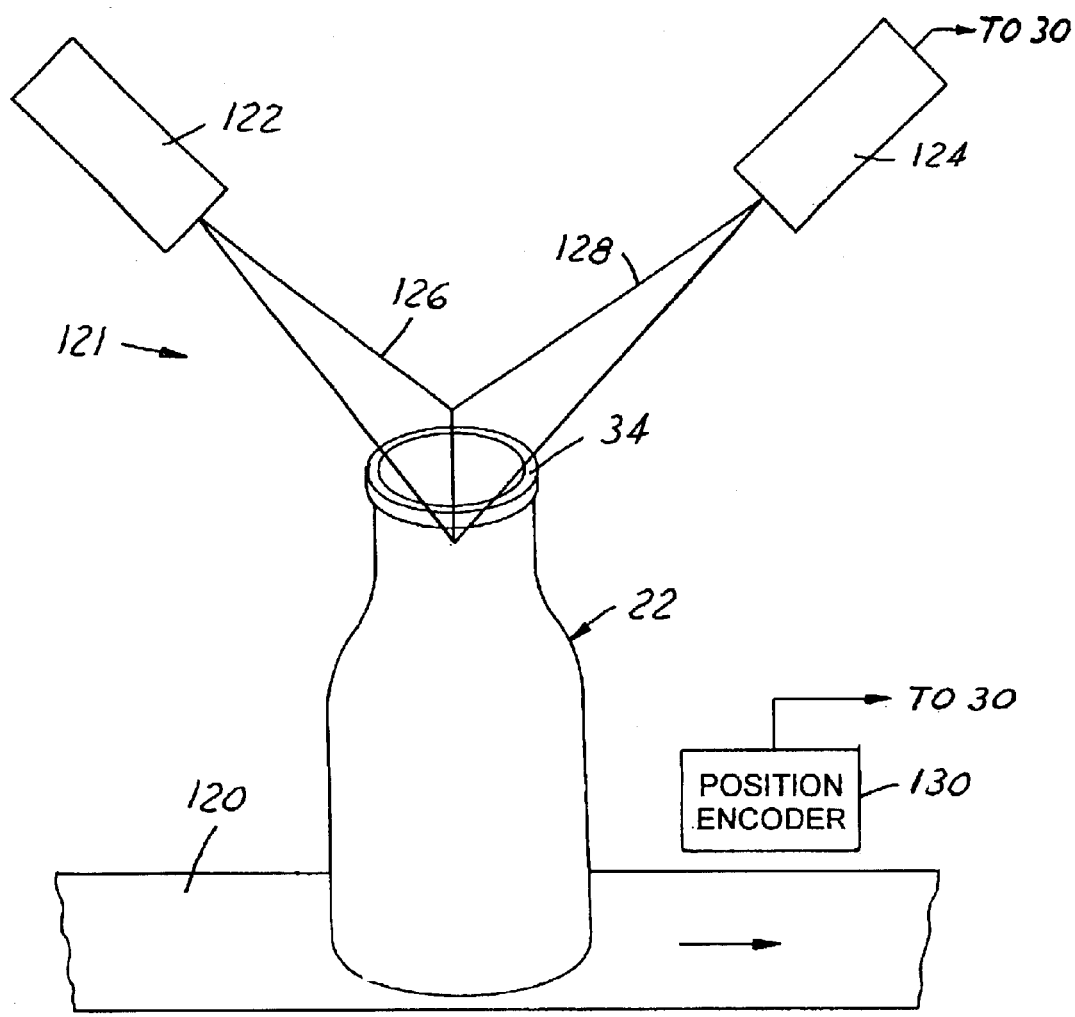
FIGS. 8A and 8B are schematic diagrams that illustrate a second embodiment of the invention as a modification to the embodiment of FIGS. 1 and 2.
Figure 8B:
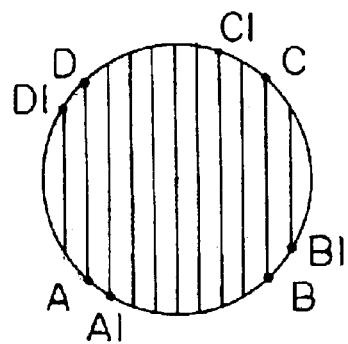

In the preferred embodiment of the invention illustrated in FIG. 1, container 22 is held in position and rotated about axis 28 during the inspection operation. Light sources 50, 54, 58, 62 are energized, and sensors 52, 56, 60, 64 are scanned by information processor 30 at spatial or temporal increments of container rotation. Thus, as the container rotates, points A–D "sweep" the sealing surface, but remain at the same nominal angular spacing from each other. An alternative arrangement is illustrated in FIGS. 8A and 8B. Container 22 is carried by a linear conveyor 120 beneath an inspection station 121 having a light source 122 and a light sensor 124. Light source 122 directs a line-shaped light beam 126 across sealing surface 34 of container 22 as the container is transported beneath the light source, and sensor 124 scans the reflected light beam 128 at increments of linear container motion. Such scanning of sensor 124 may be at equal time increments while conveyor speed is held constant, or at increments of conveyor motion as detected by a conveyor position encoder 130. Within information processor 30, the scanned information is processed to identify orthogonally spaced points A, B, C, D (FIG. 8B), and the measurement analysis proceeds accordingly. Instead of rotating the container, the information processor can in effect "rotate" the measurement points, performing the signal analysis to be described at points A, B, C, D in FIG. 8B, and then at points A1, B1, C1, D1, etc.

Figure 9:
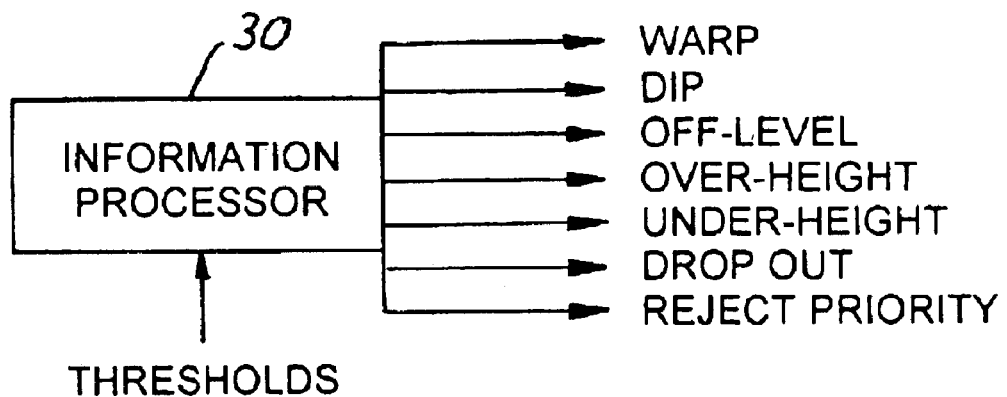
FIG. 9 is a functional block diagram of output channels from the information processor illustrated in FIG. 1.

As illustrated in FIG. 9, information processor 30 preferably provides separate output channels for indicating warp, dip, off-level, over-height and under-height measurements. Information processor 30 preferably also provides an output channel for indicating "drop out," which in general indicates failure to obtain a level measurement over all or a significant portion of the sealing surface area. A separate output channel preferably is provided for indicating "reject priority," which represents an attempt by the information processor to identify the root cause of an anomaly that provides signals on more than one of the other output channels. Information processor 30 is also adapted to receive differing thresholds selectable by an operator for each of the anomalies reflected in the various output channels.

Figure 10:
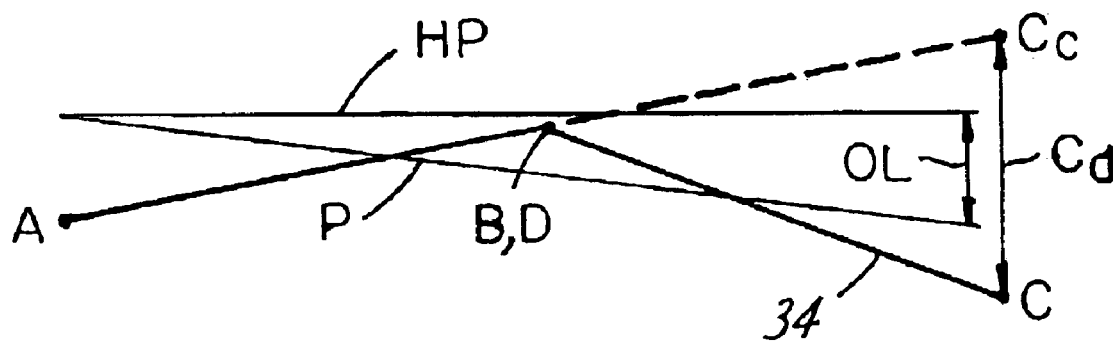
FIG. 10 is a graphic illustration useful in discussing operation of the preferred embodiments of the invention.

In general, measurement of sealing surface warp employing the four light source/sensor arrangement of FIG. 2 involves measurement of the departure of one of the measurement points—e.g., point C—from a plane defined by the other three measurement points e.g., points A, B and D. FIG. 10 illustrates a saddle-warp sealing surface situation. A plane defined by measurement points A, B and D puts the expected point C at position $C_c$. The level difference $C_d$ between measured point C and expected point $C_c$ is equal to A+C−(B+D), where A, B, C and D are the measured levels at those measurement points. Warp W at the container finish is equal to ½ ($C_{dmax}-C_{dmin}$) during container rotation. Only 180° of container rotation is necessary to obtain this measurement. If 360° of container rotation are available, then warp W can be measured twice and averaged. It will be appreciated that this measurement W contains both warp and dip because dip is similar to warp but confined to a limited angular area of the sealing surface. To separate warp information from dip information, for purposes of analysis, a dip may be identified as a warp-type signal having a limited angular extent, such as 45°. In information processor 30, dip may be separated from warp by applying a 90° rectangular convolution filter to the combined warp/dip signal for 360° of container rotation. The ratio of the unfiltered signal to the filtered signal is equal to 1 for pure warp, and is less than 1 for pure dip. By setting the threshold of the ratio at π/4 (45°), the warp component of the combined signal is separated from the dip component of the combined signal. Each component is compared to its associated threshold, and the results are provided on the corresponding "warp" and "dip" output channels (FIG. 9) for that container.

Off-level is a measure of the tilt of the average plane of the sealing surface. To measure off-level, the signals from sensors 180° apart are employed—i.e., sensors 52, 60 or sensors 56, 64 (FIG. 2). Off-level preferably is calculated for each such sensor pair—i.e., pair 52, 60 and pair 56, 64- and averaged. This technique is insensitive to variations in height at the sealing surface, but is sensitive to wobble of the container finish. To reduce wobble sensitivity, the off-level signal obtained as a function of the difference between sensors 180° apart, or the average difference of two sensor pairs, is subjected to rectangular convolution filtration over a filter length of 180°. Off-level OL is then equal to π/4 multiplied by the maximum minus the minimum of the convolution of the sensor difference signal—e.g., the convolution of $S(t)=A(t)$ minus $C(t)$. When all four sensors are used, $S(t)$ equal the average of $A(t)-C(t)$ and $B(t)-D(t)$. Thus, in FIG. 10, off-level OL is the difference between the average measured plane P of the sealing surface and the horizontal plane HP.

When performing sealing surface analysis, it is desirable to be able to identify when a sealing surface revolution has been completed. To identify one complete sealing surface revolution, a rectangular convolution filter is applied to the off-level measurement $A(t)-C(t)$ (or $B(t)-D(t)$, or an average of $A(t)-C(t)$ and $B(t)-D(t)$). The length of the convolution filter is varied upwardly and downwardly from 360°. When the output of the filter is at a minimum value, typically zero, one complete revolution of the off-level measurement signal, and therefore one complete revolution of the container sealing surface, has been identified.

It is desirable under some circumstances to be able to obtain sealing surface level variation measurement employing two measurement probes at a nominal 90° spacing from each other. This might occur in a situation in which it is desired to provide a less expensive sensor employing two rather than four measurement probes. A combined warp and off-level signal $S(t)$ is equal to $A(t)-B(t)$, where $A(t)$ and $B(t)$ are the periodic signals obtained during container rotation from sensors 52, 56 respectively. This combined signal includes both a warp component having a period of 180° and an off-level component having a period of 360°. To separate these components, a rectangular convolution filter having a length of 180° is applied to the combined signal $S(t)$. The result of this filtration is the 360° component of $S(t)$. When this 360° component is subtracted from $S(t)$, the result is the 180° component of $S(t)$. Off-level OL is equal to the maximum minus the minimum of the 360' component multiplied by the quantity $(\frac{1}{2}\sqrt{2})$. The warp component W is equal to ½ of the maximum minus the minimum of the 180° component.

Container height is measured as a function of the average of the height measurements at points A, B, C and D over a complete revolution of the container. Over-height and under-height are obtained by averaging the maximum and minimum heights respectively at points A, B, C and D over a complete revolution of the container, and comparing such average to the nominal height of the container. It is also envisioned that warp at the sealing surface can be measured employing three measurement probes—e.g., probes 42, 44 and 46–as a function of the maximum and minimum level signals at points A and B, and the average level measurement signal at point C.

It may be desirable for process control purposes to identify the correct primary reason that a container is rejected—i.e., the reject priority feature illustrated in FIG. 9. For example, the corrections required at the forming machine are different if the containers have warped finishes as compared to off-level finishes. The preferred deviation-from-a-plane method described above for measuring warp will give a signal for both warp and dip, but will measure zero for off-level. The angular extent of the deviation from a plane (e.g., greater than or less than 45°) will distinguish a warp from a dip. The off-level measurement will measure zero for pure warp, and will be only a small percentage of an actual dip value. The primary variation thus may be determined by identifying the anomaly signal of greatest value. For example, a 0.100 inch dip may also give a 0.020 inch off-level reading. However, the dip is identified as the primary commercial variation. A container with a true off-level variation will give only a small dip measurement. Warp, drip and off-level are given higher priority than under-height or over-height. If both warp and under-height produce a reject signal, for example, the container is reported as having a warp condition.

There have thus been disclosed an apparatus and method for measuring level of the sealing surface of a container that fully satisfy all of the objects and aims previously set forth. The invention has been disclosed in conjunction with a number of presently preferred embodiments thereof, and various modifications and revisions have been discussed. Other modifications and revisions will readily suggest themselves to persons of ordinary skill in the art. The invention is intended to embrace all such modifications and revisions as fall within the spirit and broad scope of the appended claims.

What is claimed is:

1. Apparatus for inspecting a container finish having an axis and an open mouth surrounded by an axially facing sealing surface, said apparatus including:

at least one light source for directing light energy onto the sealing surface of a container, at least one light sensor disposed to receive light energy reflected from the sealing surface of the container, and responsive to such reflected light energy to provide signals indicative of level of the sealing surface at at least four predetermined points on said sealing surface spaced from each other around said axis, and an information processor responsive to said signals for detecting variations in level at the sealing surface of the container, wherein said information processor is constructed to determine warp or dip at the container sealing surface as a function of departure of one of said four predetermined points from a plane-defined by the other three of said predetermined points.

2. The apparatus set forth in claim 1 wherein said information processor is responsive to said signals for detecting warp, dip, off-level and height variations at the sealing surface.

3. The apparatus set forth in claim 1 wherein said information processor is constructed to scan said at least one sensor and increments of container motion.

4. The apparatus set forth in claim 3 wherein said increments of container motion comprise increments of container rotation.

5. The apparatus set forth in claim 3 wherein said increments of container motion comprise movements of linear container motion in a direction lateral to the axis of the container finish.

6. The apparatus set forth in claim 5 wherein said at least one light source directs a line-shaped light beam entirely across the sealing surface area of the container, and said at least one sensor is disposed to receive portions of said line-shaped beam reflected from opposed positions of the container sealing surface.

7. The apparatus set forth in claim 1 wherein said information processor is constructed to differentiate between warp and dip at the container sealing surface as a function of the angular dimension around said axis of said departure from said plane.

8. The apparatus set forth in claim 1 wherein said information processor is constructed to determine off-level at the container sealing surface as a function of differences between level at ones of said predetermined points spaced 180° from each other.

9. The apparatus set forth in claim 1 wherein said information processor is constructed to scan said at least one sensor at increments of container rotation around the axis of the container finish, and to determine speed of rotation of the container as a function of signals scanned from said at least one sensor.

10. The apparatus set forth in claim 1 wherein said at least one light source includes four light sources disposed to direct light energy onto said points on the sealing surface spaced circumferentially from each other, and said at least one light sensor includes four light sensors disposed to receive light energy reflected from respective associated points on the sealing surface.

11. The apparatus set forth in claim 10 including four optical probes, each comprising one of said light sources and an associated sensor, and bracketry for mounting said four optical probes to direct light energy onto and receive reflected light energy from said four points at 90° spacing around said axis.

12. The apparatus set forth in claim 11 wherein said bracketry includes means for simultaneously adjusting all four of said probes with respect to said axis to accommodate container finishes with differing sealing surface diameters.

13. The apparatus set forth in claim 12 wherein said means includes a threaded rod coupled to a first pair of said probes, a cam coupled to a second pair of said probes, and a cam shaft operatively coupling said thread rod to said cam such that rotation of said rod varies positions of said first pair of probes oppositely of each other and simultaneously varies positions of said second pair of probes oppositely of each other.

14. Apparatus for inspecting a container finish having an axis and an open mouth surrounded by an axially facing sealing surface, which includes:
four probes each including a light source and a light sensor,
bracketry for mounting said probes above a container such that said light sources direct light energy onto the sealing surface of the container at points spaced 90° from each other around the sealing surface and said light sensors receive light energy from the associated sources reflected from the sealing surface, said light sensors providing signals indicative of level of the sealing surface at the associated points on the sealing surface,
an information processor responsive to said signals for detecting variations in level at the sealing surface of the container, and
adjustment means for adjusting radial positions of said probes equally and simultaneously with respect to the axis to accommodate differing sealing surface diameters, said adjustment means including a rod having oppositely threaded ends coupled to two of said probes such that rotation of said rod moves both of said two probes in opposite directions parallel to said rod.

15. Apparatus for inspecting a container finish having an axis and an open mouth surrounded by an axially facing sealing surface, which includes:
a first light source for directing light energy onto a first point on the sealing surface of a container, and a first light sensor for receiving light energy from said first source reflected from said first point to provide a first signal indicative of level at said first point,
a second light source for directing light energy onto a second point on the sealing surface circumferentially spaced 90° around the axis from said first point, and a second light sensor for receiving light energy from said second source reflected from said second point to provide a second signal indicative of level at said second point,
means for rotating the container such that the finish and the sealing surface rotate about said axis,
an information processor for periodically scanning said first and second light sensors to provide a periodic signal that varies as a function of said first and second signals, and information processor being adapted to separate said periodic signal into first and second components having respective periods of 180° and 360° of rotation of the finish, to determine off-level of the sealing surface as a function of said 360° component, and to determine warp of the sealing surface as a function of said 180° component.

16. Apparatus for inspecting a container finish having an axis and an open mouth surrounded by an axially facing sealing surface, which includes:
a first light source for directing light energy onto a first point on the sealing surface of a container, and a first light sensor for receiving light energy from said first source reflected at said first point to provide a signal indicative of level at said first point,
a second light source for direct said light energy onto a second point on the sealing surface circumferentially spaced around said axis from said first point, and a second light sensor for receiving light energy from said second source reflected at said second point to provide a signal indicative of level at said second point,
an information processor responsive to said signals for detecting variations in level at said first and second points on the sealing surface, and
bracketry mounting said first light source and said first sensor, and said second light source and said second sensor, above the finish of the container, said bracketry including adjustment means for simultaneously adjusting positions of said first light source and sold first sensor, and said second light source and said second sensor, with respect to said axis to accommodate inspection of container finishes of differing diameters,
wherein said first light source and said first sensor are in a first subassembly, wherein sold second light source and said second sensor are in a second subassembly, and wherein said adjustment means is constructed to adjust positions of said first and second subassemblies simultaneously and equally with respect to said axis,
wherein said adjustment means includes a rod having oppositely threaded ends respectively coupled to said subassemblies such that rotation of said rod moves both of said subassemblies in opposite directions parallel to said rod.

17. Apparatus for inspecting a container finish having an axis and an open mouth surrounded by an axially facing sealing surface, which includes:

a first light source for directing light energy onto a first point on the sealing surface of a container, And a first light sensor for receiving light energy from said first source reflected at said first point to provide a signal indicative of level at said first point, a second light source for directing said light energy onto a second point on the sealing surface circumferentially spaced around said axis from said first point, and a second light sensor for receiving light energy from said second source reflected at said second point to provide a signal indicative of level at said second point, an information processor responsive to said signals for detecting variations in level at said first and second points on the sealing surface, and bracketry mounting said first light source and said first sensor, and said second light source and said second sensor, above the finish of the container, said bracketry including adjustment means for simultaneously adjusting positions of said first light source and said first sensor, and said second light source and said second sensor, with respect to said axis to accommodate inspection of container finishes of differing diameters, wherein said first light source and said first sensor are in a first subassembly, wherein said second light source and said second sensor are in a second subassembly, and wherein said adjustment means is constructed to adjust positions of said first and second subassemblies simultaneously and equally with respect to said axis, wherein said adjustment means includes a cam plate having an axis of rotation and opposed spiral means operatively coupled to said subassemblies such that rotation of said cam plate about said axis of rotation moves both of said subassemblies in opposite directions perpendicular to said axis of rotation.

18. Apparatus for inspecting a container finish having an axis and an open mouth surrounded by an axially facing sealing surface, which includes:

four probes each including a light source and a light sensor, bracketry for mounting said probes above a container such that said light sources direct light energy onto the sealing surface of the container at points spaced 90° from each other around the sealing surface and said light sensors receive light energy from the associated sources reflected from the sealing surface, said light sensors providing signals indicative of level of the sealing surface at the associated points on the sealing surface, an information processor responsive to said signals for detecting variations in level at the sealing surface of the container, and adjustment means for adjusting radial positions of said probes equally and simultaneously with respect to the axis to accommodate differing sealing surface diameters, said adjustment means including a cam plate having an axis of rotation and opposed spiral means operatively coupled to two of said probes such that rotation of said cam plate about said axis of rotation moves said two of said probes in opposite directions perpendicular to said axis of rotation.

19. Apparatus for inspecting a container finish having an axis and an open mouth surrounded by an axially facing sealing surface, which includes:

four probes each including a light source and a tight sensor, bracketry for mounting said probes above a container such that said light sources direct light energy onto the sealing surface of the container at points spaced 90° from each other around the sealing surface and said light sensors receive light energy from the associated sources reflected from the sealing surface, said light sensors providing signals indicative of level of the sealing surface at the associated points on the sealing surface, an information processor responsive to said signals for detecting variations in level at the sealing surface of the container, and adjustment means for adjusting radial positions of said probes equally aid simultaneously with respect to the axis to accommodate differing sealing surface diameters, wherein said means includes a rod having oppositely threaded ends coupled to first paid of said probes, a cam coupled to a second pair of said probes, and a cam shaft operatively coupling said thread rod to said cam such that rotation of said rod varies positions of said first pair of robes oppositely of each other and simultaneously varies positions of said second pair of probes oppositely of each other.

20. The apparatus set forth in claim 19 wherein said cam includes a cam plate having diametrically spaced spiral openings, and said second pair of probes have pins that extend into said openings.

* * * * *